US000001552H

United States Statutory Invention Registration [19]

[11] Reg. Number: H1552

[45] Published: Jun. 4, 1996

Cain et al.

[54] PESTICIDE SUBSTITUTED DIKETONITRILES

[75] Inventors: Paul A. Cain, Cary; David T. Chou, Raleigh; Themistocles D. J. D'Silva, Chapel Hill; Daniel B. Gant, Durham; Nancy D. Herman, Cary, all of N.C.

[73] Assignee: Rhône-Poulenc Inc., Research Triangle Park, N.C.

[21] Appl. No.: 259,088

[22] Filed: Jun. 13, 1994

[51] Int. Cl.[6] ..... A01N 37/34; A61K 31/275

[52] U.S. Cl. ..... 514/521

*Primary Examiner*—Charles T. Jordan
*Assistant Examiner*—Meena Chelliah
*Attorney, Agent, or Firm*—Burns, Doane, Swecker & Mathis

[57] ABSTRACT

The invention relates to diketontrile derivatives which have been discovered useful against arthropods, plant nematodes, helminth protozoan pests or as intermediates for such useful compounds which have a general formula:

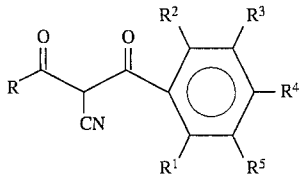

(I)

5 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PESTICIDE SUBSTITUTED DIKETONITRILES

BACKGROUND OF THE INVENTION

1. Field of the Invention

This invention relates to diketontrile derivatives, compositions containing them and their use against arthropod, plant nematode, helminth and protozoan pests, or as intermediates in the synthesis of such pesticidally active compounds.

2. Discussion of the Related Art

Herbicidal diketontriles are described in the literature, for example in European Patent Publication Nos. 0213892, 0496630 and 0496631. No insecticidal properties of such compounds are disclosed in any of these publications. It is, therefore, clear that insecticidal activity is not readily apparent from the prior art for diketontriles.

SUMMARY OF THE INVENTION

The present invention relates novel use as a pesticide of diketonitrile derivatives including their isomers and enolic tantomeric forms of formula I. The invention relates to a method for the control of pests at a locus which comprises treatment of the locus with an effective composition of formula I:

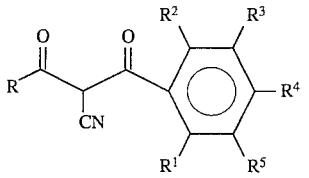

(I)

wherein:

R is:

a) straight- or branched-chain alkyl, alkenyl or alkynyl having up to six carbon atoms, optionally substituted by one or more halogen;

b) cycloalkyl having from four to six carbon atoms, optionally bearing one or more substituents selected from the group consisting of $R^6$, halogen, $—CO_2R^7$, $—SR^{71}$ and $—OR^{71}$;

c) cycloalkenyl having five or six carbon atoms, optionally bearing one or more substituents selected from the group consisting of $R^6$, halogen and $—CO_2R^7$; or d) $—(CH_2)_p$-phenyl-$(R^{21})_r$;

$R^1$ is:

hydrogen, chlorine, bromine, fluorine, methyl, methoxy or trifluoromethyl;

$R^2$, $R^3$, $R^4$ and $R^5$, each being the same or different, are:

a) hydrogen;

b) straight- or branched-chain alkyl, alkenyl or alkynyl having up to six carbon atoms, optionally substituted by one or more halogen;

c) straight- or branched-chain alkyl having up to six carbon atoms, substituted by an $—OR^6$ group;

d) halogen;

e) nitro, cyano, $—CO_2R^6$, $—COR^7$, $—X—S(O)_qR^8$, $—S(O)_nR^9$, $—O(CH_2)_mOR^6$, $—NR_{10}R^{11}$, $—CONR^{10}R^{15}$ or $—OR^{61}$;

f) cycloalkyl having from three to six carbon atoms, with the proviso that when $R^2$ is $—S(O)_nR^9$ or $OR^{61}$, then $R^9$ and $R^{61}$ cannot be cycloalkyl with three to six carbon atoms;

with the proviso that when $R^2$ is $—S(O)_nR^9$ or $OR^{61}$, then $R^9$ and $R^{61}$ cannot be cycloalkyl with three to six carbon atoms;

$R^6$ is:

a) straight- or branched-chain alkyl, alkenyl or alkynyl having up to six carbon atoms, optionally substituted by one or more halogen; or b) cycloalkyl having from three to six carbon atoms;

$R^{61}$ is:

a) straight- or branched-chain alkyl, alkenyl or alkynyl having up to six carbon atoms, optionally substituted by one or more halogen;

b) cycloalkyl having from three to six carbon atoms;

$R^7$ is:

a) straight- or branched-chain alkyl having up to six carbon atoms, optionally substituted by one or more halogen; or b) cycloalkyl having from three to six carbon atoms;

$R^{71}$ is:

straight- or branched-chain alkyl having up to three carbon atoms;

$R^8$ is:

a) straight- or branched-chain alkyl, alkenyl or alkynyl having up to six carbon atoms, optionally substituted by one or more halogen;

b) cycloalkyl having from three to six carbon atoms;

c) phenyl, optionally substituted by from one to five $R^{21}$ groups, which can be the same or different; or d) $—CH_2CN$, $—CH_2CO_2R^6$ or $—NR^{10}R^{11}$;

$R^9$ is:

a) straight- or branched-chain alkyl, alkenyl or alkynyl having up to six carbon atoms, optionally substituted by one or more halogen;

b) cycloalkyl having from three to six carbon atoms;

c) $—CH_2CN$, $—CH_2CO_2R^6$ or $NR^{10}R^{11}$;

$R^{10}$ is:

a) hydrogen;

b) straight- or branched-chain alkyl having up to six carbon atoms, optionally substituted by one or more halogen; or c) cycloalkyl having from three to six carbon atoms;

provided that when $R^7$ and $R^{10}$ are part of a group $—CONR^7R^{10}$ they can, together with the nitrogen to which they are attached, form a five or six membered ring optionally having one additional hetero ring atom which is oxygen or nitrogen, said ring being optionally substituted by one or more alkyl, each having up to three carbon atoms;

$R^{11}$ is:

a) straight- or branched-chain alkyl having up to six carbon atoms, optionally substituted by one or more halogen;

b) cycloalkyl having from three to six carbon atoms; or c) $—COR^7$, $—CO_2R^7$ or $—CONR^7R^{10}$;

provided that when $R^{10}$ and $R^{11}$ are part of a group $—NR^{10}R^{11}$ they can, together with the nitrogen to which they are attached, form a five or six membered ring optionally having one additional hetero ring atom which is oxygen or nitrogen, said ring being optionally substituted by one or more alkyl, each having up to three carbon atoms;

X is:

oxygen, $—N(R^{12})—$, $—(CR^{13}R^{14}—)_t—$ or $—S(O)^u—$;

$R^{12}$ is:

a) hydrogen;

b) straight- or branched-chain alkyl, alkenyl or alkynyl having up to six carbon atoms, optionally substituted by one or more halogen;

c) cycloalkyl having from three to six carbon atoms;

d) phenyl, optionally substituted by from one to five $R^{21}$ groups, which can be the same or different; or e) $—COR^7$, $—CO_2R^7$, $—CONR^7R^{10}$, $—OR^{17}$ or $—SO_2R^7$;

each of $R^{13}$ and $R^{14}$, which can be the same or different, is:

a) hydrogen; or b) straight- or branched-chain alkyl having up to six carbon atoms, optionally substituted by one or more halogen;

$R^{15}$ is:

$R^7$ or $—OR^{17}$;

provided that when $R^{10}$ and $R^{15}$ are part of a group $—CONR^{10}R^{15}$ they can, together with the nitrogen to which they are attached, form a five or six membered ring optionally having one additional hetero ring atom which is oxygen or nitrogen, said ring being optionally substituted by one or more alkyl, each having up to three carbon atoms;

$R^{17}$ is:

straight- or branched-chain alkyl having up to six carbon atoms;

$R^{21}$ is:

halogen, $R^7$, nitro, cyano, $—CO_2R^7$, $—S(O)_nR^7$, $—NR^{10}R^{11}$ or $—OR^7$;

m is one, two, or three;

n is zero, one or two;

p is zero or one;

q is zero, one or two; provided that when X is $—N(R^{12})—$ or oxygen, then q is two and that when X is —S(O)n—, then q is zero or two;

r is zero or an integer from one to five;

t is an integer from one to four, provided that when t is greater than one, the groups $—(CR^{13}R^{14})—$ can be the same or different; and u is zero or two;

with the proviso that when $R^1$, $R^3$, and $R^5$ are hydrogen, $R^4$ is $S(O)nR^9$ and n is two, then $R^9$ is methyl;

i) and $R^2$ is chlorine, then R is the definition other than t-butyl;

ii) and $R^2$ is trifluoromethyl, then R is other than methyl.

Also with the proviso that when $R^1$, $R^3$, and $R^5$ are hydrogen, $R^2$ is $S(O)nR^9$, n is 0, $R^9$ ii) and $R^2$ is trifluoromethyl, then R is other than methyl. is methyl, $R^4$ is chlorine, R is not 3,5-bis(trifluoromethyl)phenyl.

The following are some representative examples of preferred compound of formula I described in the examples having particularly useful pesticidal activity:

Miticidal Activity:

1-(4-chloro-2-methylsulfonylphenyl)-2-cyano-4-methylpentan-1,3-dione;

1-(4-chloro-2-nitrophenyl)-2-cyano-4-methylpentan-1,3-dione;

Insecticidal Activity:

1-(4-chloro-2-methylsulfonylphenyl)-2-cyano-4-methylpentan-1,3-dione;

1-(2-chloro-3-methoxy-4-methylsulfonylphenyl)-2-cyanobutan-1,3-dione;

2-cyano-1-(2-nitro-4-trifluoromethylphenyl)-butan-1,3-dione.

It is an object of this invention to provide a method for control of pests.

It is an object to provide a method of control of pests, especially mites, aphids, insects, plant nematodes, or soil born insects, especially for use in agricultural or horticultural crops, use in public health.

It is also an object to provide methods of making insecticidally active compositions using the compositions herein as intermediates.

These and other objects will be readily apparent from the detailed description presented herein.

Processes for Preparation

Compounds of formula I are known or may be prepared using known methods, for example as described in European Patent Publication Nos. 0213892, 0496630 and 0496631.

Brief Process Section

For example compound of formula (I) may be prepared from a compound of formula (II):

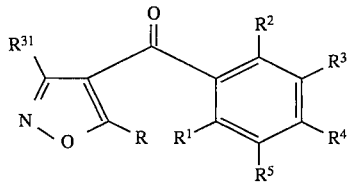

(II)

or of formula (III):

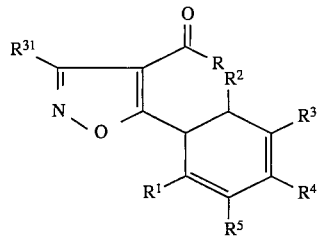

(III)

wherein R, $R^1$, $R^2$, $R^3$, $R^4$ and $R^5$ are as defined above and $R^{31}$ represents the hydrogen atom or a group selected from a carboxylic ester, amide, nitrile and acyl.

Where $R^{31}$ represents hydrogen or an acyl group the reaction is carried out by treatment with a base. Examples of suitable bases include alkali or alkaline earth metal hydroxides or alkoxides such as sodium ethoxide or organic bases such as triethylamine.

Where $R^{31}$ represents a group such as an ester, amide or nitrile the conversion is carried out by a hydrolytic reaction. The hydrolyric reaction may be carried out in the presence of an acid or base. Acidic hydrolysis may be achieved for example using aqueous hydrochloric acid. Basic hydrolysis may be achieved for example using sodium hydroxide in a mixture of alcohol and water. The reactions are carried out at a temperature between room temperature and the reflux temperature of the mixture.

Compounds of formula (I) may also be prepared by the reaction of a benzoyl chloride of formula (IV):

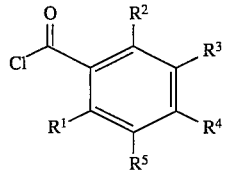

(IV)

wherein R, $R^1$, $R^2$, $R^3$, $R^4$ and $R^5$ are as hereinbefore defined, with a beta-ketronitrile of formula (V):

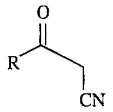

(V)

wherein R is as hereinbefore defined. The reaction is generally performed in the presence of a base in a solvent or solvent mixture. Suitable bases include metal hydrides, hydroxides or alkoxides (e.g. sodium or lithium hydride, sodium hydroxide, potassium hydroxide, magnesium ethoxide or magnesium methoxide). Suitable solvents include for example tetrahydrofuran; hydrocarbons such as toluene; or halogenated hydrocarbons such as dichloromethane. The reaction is generally performed at a temperature from 0° C. to reflux temperature.

The compounds of formula (I) may also be prepared by the reaction of an acid chloride of formula (VI):

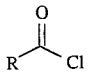

(VI)

wherein R is as hereinbefore defined, with a beta-ketonitrile of formula (VII):

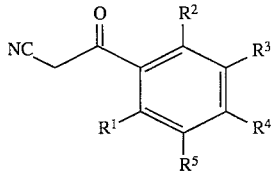

(VII)

wherein R, $R^1$, $R^2$, $R^3$, $R^4$ and $R^5$ are as hereinbefore defined. The reaction is generally performed in the presence of a base in a solvent or solvent mixture. Suitable bases include metal hydrides, hydroxides or alkoxides (e.g. sodium or lithium hydride, sodium hydroxide, potassium hydroxide, magnesium ethoxide or magnesium methoxide). Suitable solvents include for example tetrahydrofuran; hydrocarbons such as toluene; or halogenated hydrocarbons such as dichloromethane. The reaction is generally performed at a temperature from 0° C. to reflux temperature.

Compounds of formula (II), (III), (IV), (V), (VI) and (VII) are known or may be prepared by known methods. For example compounds of formula (II), (III) and (IV) are described in European Patent Publication numbers 0418175, 0487357 and 0524018.

Compound of formulae I are known or may be prepared by the application of known methods, such as those described in the publication numbers described above.

A feature of the present invention therefore provides a method of control of pests at a locus which comprises the treatment of the locus (e.g., by application or administration) with an effective amount of a compound of formula I, wherein the substituent groups are as hereinbefore defined. The locus includes, for example, the pest itself or the place (plant, animal, person, field, structure, premises, forest, orchard, waterway, soil, plant or animal product, or the like) where the pest resides or feeds.

The compounds of this invention are useful in the control via foliar application or systemic action of some arthropods, especially some insects, which feed on the above ground portions of plants. Control of foliar pests may additionally be provided by application to the plant roots or plant seeds with subsequent systemic translocation to the above ground portions of the plants.

The compounds of this invention may be useful to control soil insects, such as corn rootworm, termites (especially for protection of structures), root maggots, wireworms, root weevils, stalkborers, cutworms, root aphids, or grubs. They may also be used to provide activity against plant pathogenic nematodes, such as root-knot, cyst, dagger, lesion, or stem or bulb nematodes, or against mites. For the control of soil pests, for example corn rootworm, the compounds are advantageously applied to or incorporated at an effective rate into the soil in which crops are planted or to be planted or to the seeds or growing plant roots.

In the area of public health, the compounds are especially useful in the control of many insects, especially filth flies or other Dipteran pests, such as houseflies, stableflies, soldierflies, hornflies, deerflies, horseflies, midges, punkies, blackflies, or mosquitoes.

Compounds of the invention may be used in the following applications and on the following pests including arthropods, especially insects or mites, nematodes, or helminth or protozoan pests:

The invention, as previously described, provides methods of control of pests via application or administration of an effective amount of compounds of formula I at a locus which comprises treatment of the locus.

In practical use for the control of arthropods, especially insects or mites, or nematode pests of plants, a method, for example, comprises applying to the plants or to the medium in which they grow an effective amount of a compound of the invention. For such a method, the active compound is generally applied to the locus in which the arthropod or nematode infestation is to be controlled at an effective rate in the range of about 0.005 kg to about 15 kg of the active compound per hectare of locus treated. Under ideal conditions, depending on the pest to be controlled, a lower rate may offer adequate protection. On the other hand, adverse weather conditions, resistance of the pest or other factors may require that the active ingredient be used at higher rates. The optimum rate depends usually upon a number of factors, for example, the type of pest being controlled, the type or the growth stage of the infested plant, the row spacing or also the method of application. More preferably an effective rate range of the active compound is from about 0.01 kg/ha to about 2 kg/ha.

When a pest is soil-borne, the active compound generally in a formulated composition, is distributed evenly over the area to be treated (i.e., for example broadcast or band treatment) in any convenient manner. Application may be made, if desired, to the field or crop-growing area generally or in close proximity to the seed or plant to be protected from attack. The active component can be washed into the soil by spraying with water over the area or can be left to the natural action of rainfall. During or after application, the formulated compound can, if desired, be distributed mechanically in the soil, for example by ploughing, disking, or use of drag chains. Application can be prior to planting, at planting, after planting but before sprouting has taken place, or after sprouting. Additionally, a method of control may also comprise treatment of the seed prior to planting with subsequent control effected after planting the seed.

Methods of control of pests also consist of application to or treatment of the foliage of plants to control arthropods, especially insects or mites, or nematodes attacking the aerial parts of the plants. In addition, methods of control of pests by the invention compounds are provided to control pests which feed on parts of the plant remote from the point of application, e.g., leaf feeding insects which are controlled via systemic action of the active compound when applied for example to the roots of a plant or to the plant seed prior to planting. Furthermore, the compounds of the invention may reduce attacks on a plant by means of antifeeding or repellent effects.

The compounds of the invention and methods of control of pests therewith are of particular value in the protection of field, forage, plantation, glasshouse, orchard or vineyard crops, of ornamentals, or of plantation or forest trees, for example: cereals (such as maize, wheat, rice, or sorghum), cotton, tobacco, vegetables (such as beans, cole crops, curcurbits, lettuce, onions, tomatoes or peppers), field crops (such as potatoes, sugar beets, ground nuts, soybeans, or oil seed rape), sugar cane, grassland or forage crops (such as maize, sorghum, or lucerne), plantations (such as tea, coffee, cocoa, banana, palm oil, coconut, rubber, or spices), orchards or groves (such as of stone or pit fruit, citrus, kiwifruit, avocado, mango, olives or walnuts), vineyards, ornamental plants, flowers or vegetables or shrubs under glass or in gardens or parks, or forest trees (both deciduous and evergreen) in forests, plantations or nurseries.

They are also valuable in the protection of timber (standing, felled, converted, stored or structural) from attack, for example, by sawflies or beetles or termites.

They have applications in the protection of stored products such as grains, fruits, nuts, spices or tobacco, whether whole, milled or compounded into products, from moth, beetle, mite or grain weevil attack. Also protected are stored animal products such as skins, hair, wool or feathers in natural or converted form (e.g. as carpets or textiles) from moth or beetle attack as well as stored meat, fish or grains from beetle, mite or fly attack.

Additionally, the compounds of the invention and methods of use thereof are of particular value in the control of arthropods, helminths or protozoa which are injurious to, or spread or act as vectors of diseases in man and domestic animals, for example those hereinbefore mentioned, and more especially in the control of ticks, mites, lice, fleas, midges, or biting, nuisance or myiasis flies. The compounds of the invention are particularly useful in controlling arthropods, helminths or protozoa which are present inside domestic host animals or which feed in or on the skin or suck the blood of the animal, for which purpose they may be administered orally, parenterally, percutaneously or topically.

METHOD OF USE OF INSECTICIDAL COMPOUNDS

The following representative test procedures, using compounds of the invention, were conducted to determine the pesticidal use and activity of compounds of the invention against: mites; certain insects, including aphids, a species of caterpillar, a fly, a beetle larvae and a nematode. The specific species tested were as follows:

| GENUS, SPECIES | COMMON NAME | (ABBREVATION) |
|---|---|---|
| *Tetranychus urticae* | twospotted spider mite | TSM |
| *Aphis nasturtii* | Buckthorn aphid | BA |
| *Aphis gossypii* | Cotton aphid | CA |
| *Spdoptera eridania* | Southern armyworm | SAW |
| *Musca domestica* | House fly | HF |
| *Epilachna varivestis* | Mexican bean beetle | MBB |
| *Meloidogyne incognita* | southern root-knot nematode | SRKN |

Formulations:

The test compounds were formulated for use according to the following methods.

For mite, aphids, southern armyworm and Mexican bean beetle, a solution or suspension was prepared by adding 50 mg of the test compound to a solution of 160 mg of dimethylformamide, 838 mg of acetone, 2 mg of a 3:1 ratio of Triton X-172: Triton X-152 (respectively, mainly anionic and nonionic low foam emulsifiers which are each anhydrous blends of alkylaryl polyether alcohols with organic sulfonates), and 98.99 g of water. The result was a concentration of 500 ppm of the test compound.

For house fly tests, the formulation was initially prepared in a similar manner to the above, but in 16.3 g of water with corresponding adjustment of other components, providing a 1000 ppm concentration. Final dilution with an equal volume of a 20% by weight aqueous solution of sucrose provided a 500 ppm concentration of the test compound. When necessary, sonication was provided to insure complete dispersion.

For southern root-knot nematode tests, a stock solution or suspension was prepared by adding 10 mg of the test compound to 200 mg of dimethylformamide, 600 mg of acetone and 1.5 mg of the emulsifier blend referenced above. Water was then added to provide a test compound concentration of 166 ppm. When necessary, sonication was provided to insure complete dispersion.

Test Procedures:

The above formulated test compounds were then evaluated for their pesticidal activity at the specified concentrations, in ppm (parts per million) by weight, according to the following test procedures:

Twospotted spider mite: Leaves infested with adult and nymphal stages of the two-spotted spider mite, obtained from a stock culture were placed on the primary leaves of two bean plants growing in a 6 cm. peat pot. A sufficient number of mites (150–200) for testing were transferred to the fresh plants within a period of twenty-four hours. The potted plants (one pot per compound) were placed on a revolving turntable and sprayed, sufficient to wet the plants to runoff, with 50 ml of the 500 ppm test compound formulation by use of a DeVilbiss spray gun set at 40 psig. air pressure. As an untreated control, 50 ml of the water-acetone-DMF-emulsifier solution, containing no test compound, were also sprayed on infested plants. A treated control with a commercial technical compound, either dicofol or hexythiazox, formulated in the same manner, was tested as a standard. The sprayed plants were held for six days, after which a mortality count of motile forms was made.

Twospotted spider mite (ovicide test): Eggs were obtained from adults of the twospotted spider mite from a stock culture. Heavily infested leaves from the stock culture were placed on uninfested bean plants. Females were allowed to oviposit for a period of about 24 hours, after which the leaves of the plant were dipped into a solution of TEPP (tetraethyl diphosphate) in order to kill the motile forms and prevent additional egg laying. This dipping procedure, which was repeated after the plants dried, did not affect the viability of the eggs. The potted plants (one pot per compound) were placed on a revolving turntable and sprayed, sufficient to wet the plants to runoff, with 50 ml of the 500 ppm test compound formulation by use of a DeVilbiss spray gun set at 40 psig. air pressure. As an untreated control, 50 ml of the water-acetone-DMF-emulsifier solution, containing no test compound, were also sprayed on infested plants. A treated control with a commercial technical compound, typically demeton, formulated in the same manner, was tested as a standard. The sprayed plants were held for seven days, after which a mortality count of egg forms was made along with notations on residual activity on hatched larvae.

Buckthorn or cotton aphid: Adult and nymphal stages of buckthorn or cotton aphid were reared on potted dwarf nasturtium or cotton plants, respectively. The potted plants (one pot per compound tested) infested with 100–150 aphids, were placed on a revolving turntable and sprayed with 50 ml of the 500 ppm test compound formulation by use of a DeVilbiss spray gun set at 40 psig air pressure. As an untreated control, 50 ml of a water-acetone-DMF-emulsifier solution, containing no test compound, were also sprayed on infested plants. A treated control with a commercial technical compound, malathion or cyhalothrin, formulated in the same manner, was tested as a standard. After spraying, the pots were stored for one day for buckthorn aphid or three days for cotton aphid, after which the dead aphids were counted.

Southern armyworm: Potted bean plants, were placed on a revolving turntable and sprayed with 50 ml of the 500 ppm test compound formulation by use of a DeVilbiss spray gun set at 40 psig air pressure. As an untreated control, 50 ml of a water-acetone-DMF-emulsifier solution, containing no test compound, were also sprayed on plants. A treated control with a commercial technical compound, either cypermethrin or sulprofos, formulated in the same manner, was tested as a standard. When dry, the leaves were placed in plastic cups lined with moistened filter paper. Five randomly selected second instar southern armyworm larvae were introduced into each cup which was closed and held for five days. Larvae which were unable to move the length of the body, even upon stimulation by prodding, were considered dead.

Mexican bean beetle: Potted bean plants were placed on a revolving turntable and sprayed with 50 ml of the 500 ppm test compound formulation, sufficient to wet the plants to runoff, by use of a DeVilbiss spray gun set at 40 psig air pressure. As an untreated control, 50 ml of a water-acetone-DMF-emulsifier solution, containing no test compound, were also sprayed on plants. A treated control with a commercial technical compound, either cypermethrin or sulprofos, formulated in the same manner, was tested as a standard. When dry, the leaves were placed in plastic cups lined with moistened filter paper. Five randomly selected second instar Mexican bean beetle larvae were introduced into each cup which was closed and held for five days. Larvae which were unable to move the length of the body, even upon stimulation by prodding, were considered dead.

House fly: Four to six day old adult house flies were reared according to the specifications of the Chemical Specialties Manufacturing Association (Blue Book, McNair-Dorland Co., N.Y. 1954; pages 243–244, 261) under controlled conditions. The flies were immobilized by anesthetizing with carbon dioxide and twenty five immobilized individuals, males and females, were transferred to a cage consisting of a standard food strainer and a wrapping-paper-covered surface. Ten ml of the 500 ppm test compound formulation were added to a soufflé cup containing an absorbent cotton pad. As an untreated control, 10 ml of a water-acetone-DMF-emulsifier - sucrose solution, containing no test compound, were applied in a similar manner. A treated control with a commercial technical compound, malathion, formulated in the same manner, was tested as a standard. The bait cup was introduced inside the food strainer prior to admitting the anesthetized flies. After 24 hours, flies which showed no sign of movement on stimulation were considered dead.

Southern root-knot nematode: Infected roots of tomato plants, containing egg masses of southern root-knot nematode, were removed from a stock culture and cleaned of soil by shaking and washing with tap water. The nematode eggs were separated from the root tissue and rinsed with water. Samples of the egg suspension were placed on a fine screen over a receiving bowl, in which the water level was adjusted to be in contact with the screen. From the bowl, juveniles were collected on a fine screen. The bottom of a cone-shaped container was plugged with coarse vermiculite and then filled to within 1.5 cm of the top with about a 200 ml volume of pasteurized soil. Then into a hole made in the center of the soil in the cone was pipeted an aliquot of the 150 ppm test compound formulation. A treated control with a commercial technical compound, fenamiphos, formulated in a similar manner, was tested as a standard. As an untreated control, an aliquot of a water-acetone-DMF-emulsifier solution, containing no test compound, was applied in a similar manner. Immediately after treatment of the soil with the test compound there were added to the top of each cone 1000 second stage juvenile southern root-knot nematodes. After 3 days, a single healthy tomato seedling was then transplanted into the cone. The cone, containing the infested soil and tomato seedling, was kept in the greenhouse for 3 weeks. At the termination of the test, roots of the tomato seedling were removed from the cone and evaluated for galling on a rating scale relative to the untreated control as follows:

1- severe galling, equal to untreated control 3- light galling 4- very light galling 5- no galling, i.e., complete control These results were then converted to an $ED_3$ or $ED_5$ value (effective dose to provide a 3 or 5 gall rating).

Test Results

The above procedures were used to evaluate a number of compounds within the scope of the invention. The following compounds in Table I were active against 1 or more insects described above up to 100% mortality. Mites, aphids, southern armyworm, Mexican bean beetle, cotton aphid and house fly were tested at 500 ppm; nematodes at 21 kg/ha.

TABLE 1

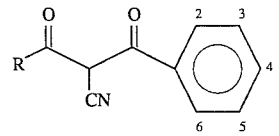

| R | BENZSUB |
|---|---|
| Me | 2-Cl-3-OMe-4-SO2Me |
| Me | 2-NO2-4-CF3 |
| tBu | 2-NO2-4-CF3 |
| iPr | 2-NO2-4-Cl |
| iPr | 2-SO2Me-4-Cl |

Compounds of formula (I) may be prepared by the application or adaptation of known methods (i.e. methods heretofore used or described in the literature), for example as hereinafter described.

In the following description where symbols appearing in formulae are not specifically defined, it is to be understood that they are "as hereinbefore defined" in accordance with the first definition of each symbol in the specification.

It is to be understood that in the descriptions of the following processes the sequences may be performed in different orders, and that suitable protecting groups may be required to achieve the compounds sought.

According to a feature of the present invention compounds of formula (I) may be prepared from a compound of formula (II):

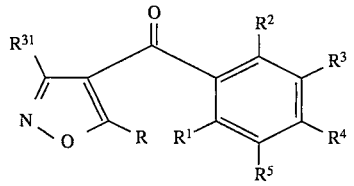

(II)

wherein R, $R^1$, $R^2$, $R^3$, $R^4$ and $R^5$ are as hereinbefore defined and $R^{31}$ represents the hydrogen atom or a group selected from a carboxylic ester, amide, nitrile and acyl.

Where $R^{31}$ represents hydrogen or an acyl group the reaction is carried out by treatment with a base. Examples of suitable bases include alkali or alkaline earth metal hydroxides or alkoxides such as sodium ethoxide or organic bases such as triethylamine.

Where $R^{31}$ represents a group such as an ester, amide or nitrile the conversion is carried out by a hydrolyric reaction. The hydrolyric reaction may be carried out in the presence of an acid or base. Acidic hydrolysis may be achieved for example using aqueous hydrochloric acid. Basic hydrolysis may be achieved for example using sodium hydroxide in a mixture of alcohol and water. The reactions are carried out at a temperature between room temperature and the reflux temperature of the mixture.

The present invention compounds of formula (I) may be prepared from a compound of formula (III)

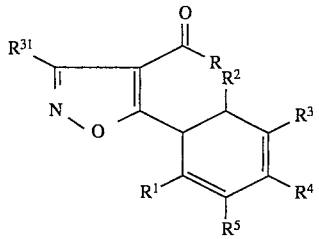

(III)

wherein R, $R^1$, $R^2$, $R^3$, $R^4$, $R^5$ and $R^{31}$ are as hereinbefore defined.

Where $R^{31}$ represents hydrogen or an acyl group the reaction is carried out by treatment with a base. Examples of suitable bases include alkali or alkaline earth metal hydroxides or alkoxides such as sodium ethoxide or organic bases such as triethylamine.

Where $R^{31}$ represents a group such as an ester, amide or nitrile the conversion is carried out by a hydrolytic reaction. The hydrolytic reaction may be carried out in the presence of an acid or base. Acidic hydrolysis may be achieved for example using aqueous hydrochloric acid. Basic hydrolysis may be achieved for example using sodium hydroxide in a mixture of alcohol and water. The reactions are carried out at a temperature between room temperature and the reflux temperature of the mixture.

Further the present compounds of formula (I) may also be prepared by the reaction of a benzoyl chloride of formula (IV):

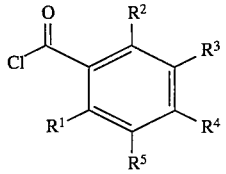

(IV)

wherein $R^1$, $R^2$, $R^3$, $R^4$ and $R^5$ are as hereinbefore defined, with a beta-ketonitrile of formula (V):

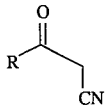

(V)

wherein R is as hereinbefore defined. The reaction is generally performed in the presence of a base in a solvent or solvent mixture. Suitable bases include metal hydrides, hydroxides or alkoxides (e.g. sodium or lithium hydride, sodium hydroxide, potassium hydroxide, magnesium ethoxide or magnesium methoxide). Suitable solvents include for example tetrahydrofuran; hydrocarbons such as toluene; or halogenated hydrocarbons such as dichloromethane. The reaction is generally performed at a temperature from 0° C. to reflux temperature.

The compounds of formula (I) may also be prepared by the reaction of an acid chloride of formula (VI):

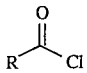

(VI)

wherein R is as hereinbefore defined, with a beta-ketonitrile of formula (VII):

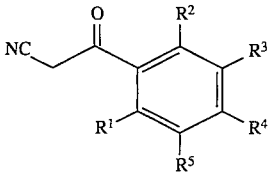

(VII)

wherein $R^1$, $R^2$, $R^3$, $R^4$ and $R^5$ are as hereinbefore defined. The reaction is generally performed in the presence of a base in a solvent or solvent mixture. Suitable bases include metal hydrides, hydroxides or alkoxides (e.g. sodium or lithium hydride, sodium hydroxide, potassium hydroxide, magnesium ethoxide or magnesium methoxide). Suitable solvents include for example tetrahydrofuran; hydrocarbons such as toluene; or halogenated hydrocarbons such as dichloromethane. The reaction is generally performed at a temperature from 0° C. to reflux temperature.

The present invention compounds of formula (I) may be prepared by the reaction of a benzoyl chloride of formula (IV) wherein $R^1$, $R^2$, $R^3$, $R^4$ and $R^5$ are as hereinbefore defined, with a beta-ketonitrile of formula (V) wherein R is as hereinbefore defined, via an intermediate of formula (VIII):

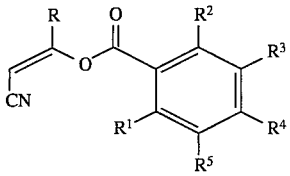

(VIII)

wherein R, $R^1$, $R^2$, $R^3$, $R^4$ and $R^5$ are as hereinbefore defined. The formation of the intermediate of formula (VIII) may be carried out in the presence of a mild base such as an organic base, e.g. triethylamine, in an inert solvent such as acetonitrile or dichloromethane at a temperature between room temperature and the reflux temperature of the mixture. The rearrangement of the intermediate of formula (VIII) to a compound of formula (I) may be carried out optionally in situ in an inert solvent such as acetonitrile or dichloromethane in the presence of a catalyst such as a source of cyanide. Examples of such sources of cyanide are acetone cyanhydrin or an alkali metal cyanide such as potassium cyanide, optionally in the presence of a crown ether such as 18-crown-6.

The present invention compounds of formula (I) may be prepared by the reaction of an acid chloride of formula (VI) wherein R is as hereinbefore defined, with a beta-ketonitrile of formula (VII) wherein $R^1$, $R^2$, $R^3$, $R^4$ and $R^5$ are as hereinbefore defined via an intermediate of formula chloride of formula (VI) wherein R is as hereinbefore defined, with a beta-ketonitrile of formula (IX):

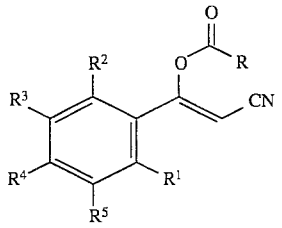

(IX)

wherein R, $R^1$, $R^2$, $R^3$, $R^4$ and $R^5$ are as hereinbefore defined. The formation of the intermediate of formula (IX) may be carried out in the presence of a mild base such as an organic base, e.g. triethylamine, in an inert solvent such as acetonitrile or dichloromethane at a temperature between room temperature and the reflux temperature of the mixture. The rearrangement of the intermediate of formula (IX) to a compound of formula (I) may be carried out optionally in situ in an inert solvent such as acetonitrile or dichloromethane in the presence of a catalyst such as a source of cyanide. Examples of such sources of cyanide are acetone cyanhydrin or an alkali metal cyanide such as potassium cyanide, optionally in the presence of a crown ether such as 18-crown-6.

Intermediates in the preparation of compounds of formula (I) may be prepared by the application or adaptation of known methods.

Compounds of formula (II) or (III) in which R31 represents hydrogen may be prepared by the reaction of a compound of formula (X):

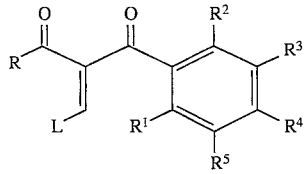

(X)

wherein $R^1$, $R^2$, $R^3$, $R^4$ and $R^5$ are as hereinbefore defined and L is —$OR^{72}$ or —$N(R^{72})_2$ and $R^{72}$ is an alkyl group, with a salt of hydroxylamine in the presence of a base or acid acceptor. The reaction is generally carried out using hydroxylamine hydrochloride in the presence of sodium acetate or an acetate or an organic base such as triethylamine. The reaction is preferably performed in a solvent. Suitable solvents include alcohols such as ethanol or inert solvents such as acetonitrile. The reaction is carried out at a temperature between room temperature and the boiling point of the solvent.

Compounds of formula (X) in which L represents —$OR^{72}$ may be prepared by the reaction of a diketone of formula (XI):

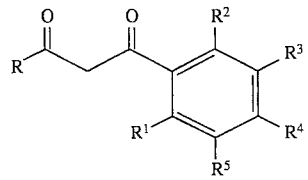

(XI)

wherein R, $R^1$, $R^2$, $R^3$, $R^4$ and $R^5$ are as hereinbefore defined, with an ortho ester, $HC(OR^{72})_3$. The reaction is generally carried out using triethyl orthoformate in the presence of an acid catalyst such as acetic anhydride. The reaction is carried out at a temperature between room temperature and the boiling point of the mixture.

Compounds of formula (X) in which L represents —$N(R^{72})_2$ may be prepared by the reaction of a diketone of formula (XI) with an amide acetal of formula $(R^{72})_2N$—$CH(OR^{72})_2$. The reaction is optionally carried out in an inert solvent such as toluene at a temperature between room temperature and the boiling point of the mixture.

Compounds of formula (II) wherein $R^{31}$ represents an ester, nitrile or acyl group may be prepared by the reaction of a compound of formula (XII):

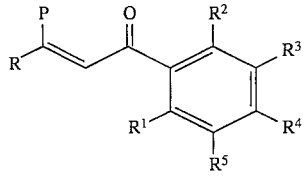

(XII)

wherein R, $R^1$, $R^2$, $R^3$, $R^4$ and $R^5$ are as hereinbefore defined and P is a leaving group such as N,N-dialkylamino, with a compound of formula $R^{31}$—C(Z)=NOH wherein $R^{31}$ represents an ester, nitrile or acyl group and Z is a halogen atom. Generally Z is a chlorine or bromine atom. The reaction is generally performed in an inert solvent such as toluene or dichloromethane either in the presence of a base such as triethylamine or a catalyst such as a 4 Angstrom molecular sieve or fluoride ion.

Compounds of formula (XII) may be prepared by the reaction of a compound of formula ($CH_2$=$C(R^{31})$(P), wherein $R^{31}$ and P are as hereinbefore defined, with a benzoyl chloride of formula (IV). The reaction is generally carried out in the presence of an organic base such as triethylamine in an inert solvent such as toluene or dichloromethane at a temperature between −20° C. and room temperature.

Compounds of formula (II) or (III) wherein $R^{31}$ represents an ester, nitrile or acyl group may be prepared by the reaction of a compound of formula (XI) with a compound of formula $R^{31}$—C(Z)=NOH wherein $R^{31}$ represents an ester, nitrile or acyl group and Z is as hereinbefore defined. Generally Z is a chlorine or bromine atom. The reaction is generally performed in an inert solvent such as dichloromethane or acetonitrile in the presence of a base. Examples of suitable bases are alkaline earth metal alkoxides such as magnesium methoxide and the reaction is carried out at a temperature between room temperature and the reflux temperature of the mixture.

Compounds of formula (II) or (III) wherein $R^{31}$ represents an amide group may be prepared by the reaction of the corresponding compound of formula (II) or (III) in which $R^{31}$ represents and ester group with ammonia or an amine. The reaction is carried out in a solvent or solvent mixture such as aqueous ethanol at a temperature between room temperature and the reflux temperature of the mixture.

Compounds of formula (III) in which $R^{31}$ represents hydrogen may be prepared by the reaction of a compound of formula (XIII):

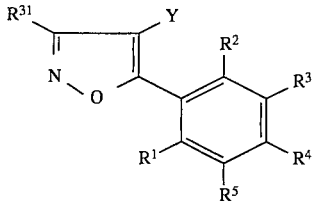

(XIII)

in which $R^{31}$ represents hydrogen and Y represents a carboxy group, or a reactive derivative thereof (such as a carboxylic acid chloride or carboxylic ester) or a cyano group, with an appropriate organometallic reagent such as a Grignard reagent or an organolithium reagent, to introduce the group —COR into the 4-position of the isoxazole ring. The reaction is generally carried out in an inert solvent such as ester or tetrahydrofuran, at a temperature from 0° C. to the reflux temperature of the solvent.

Compounds of formula (III) in which $R^{31}$ is an ester, nitrile or acyl group may be prepared by the reaction of a compound of formula (XIV):

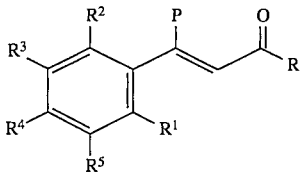

(XIV)

wherein P is a leaving group such as N,N-dialkylamino with a compound of formula $R^{31}C(Z)=N—OH$ wherein Z is as hereinbefore defined and $R^{31}$ is an ester, nitrile or acyl group. Generally Z is chlorine or bromine. The reaction is generally performed in an inert solvent such as toluene or dichloromethane either in the presence of a base such as triethylamine or a catalyst such as a 4A molecular sieve or fluoride ion.

Compounds of formula (XIII) in which $R^{31}$ is a hydrogen atom and Y is —$CO_2$-alkyl or —CN may be prepared by the reaction of a compound of formula (XV):

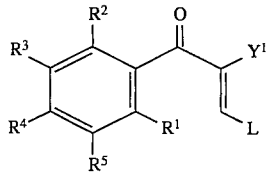

(XV)

wherein $Y^1$ represents $CO_2$-alkyl or —CN and L is as hereinbefore described, with a salt of hydroxylamine such as hydroxylamine hydrochloride, in a solvent such as ethanol or acetonitrile, optionally in the presence of a base or acid acceptor such as triethylamine or sodium acetate.

Compounds of formula (XIII) in which $R^{31}$ represents hydrogen and Y represents a carboxylic acid or carboxylic acid chloride may be prepared from the corresponding compound of formula (XIII) in which $R^{31}$ represents hydrogen and Y represents a carboxylic ester group by the hydrolysis of said ester group and conversion, as necessary, of the acid thus obtained to the acid chloride, e.g. by heating with thionyl chloride.

Compounds of formula (XV) may be prepared by the reaction of a compound of formula (VII) or a ketoester of formula (XVI):

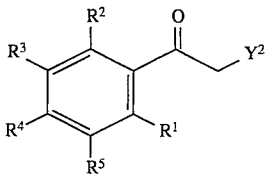

(XVI)

wherein $R^1$, $R^2$, $R^3$, $R^4$ and $R^5$ are as hereinbefore defined and $Y^2$ represents —$CO_2$-alkyl, with either triethyl orthoformate in the presence of acetic anhydride at the reflux temperature of the mixture or with dimethylformamide dimethylacetal optionally in an inert solvent such as toluene at a temperature from room temperature to the reflux temperature of the mixture.

Compounds of formula (XIV) may be prepared by the reaction of a compound of formula (XVII):

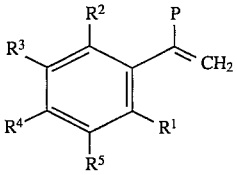

(XVII)

wherein $R^1$, $R^2$, $R^3$, $R^4$, $R^5$ and P is as hereinbefore defined, with an acid chloride of formula (VI) wherein R is as hereinbefore defined, in an inert solvent such as dichloromethane or toluene, in the presence of a base such as triethylamine.

Acid chlorides of formula (IV) or (VI) are generally known or can be prepared from the corresponding carboxylic acid according to commonly accepted methods, for example by using thionyl chloride in chloroform at reflux.

Beta-ketonitriles of formula (V) may be prepared from acid chlorides of formula (VI) by a number of methods well known in the chemical literature. For example, see Krauss, et al., Synthesis, 1983, 308, or Muth, et al., J. Org. Chem. 1960, 25, 736. Alternatively beta-ketonitriles of formula (V) may be prepared by the reaction of an ester of formula R—$CO_2$Et, wherein R is as hereinbefore defined, with acetonitrile. This reaction is described in the literature for example see the article by Abramovitch and Hauser, J. Am. Chem. Soc., 1942, 64, 2720.

Beta-ketonitriles of formula (VII) may be prepared from benzoyl chlorides of formula (IV) or from ethyl benzoates of formula (XVIII):

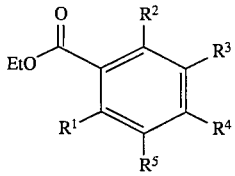

(XVIII)

wherein $R^1$, $R^2$, $R^3$, $R^4$ and $R^5$ are as hereinbefore defined, in a manner analogous to the preparation of beta-ketonitriles of formula (V) set forth above.

Compounds of formula (V), (XI), (XIV), (XVI), (XVII) and (XVIII) are known or may be prepared by the application and adaptation of known methods.

Agriculturally acceptable salts and metal complexes of compounds of formula (I) may be prepared by known methods.

What is claimed is:

1. A method of controlling insects, aphids, mites, or nematodes at a locus which comprises treatment of the locus with an effective amount of a compound of the formula:

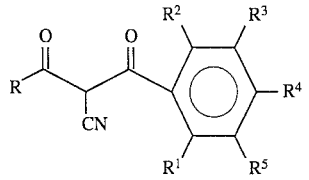

(I)

wherein:

R is:

a) straight- or branched-chain alkyl, alkenyl or alkynyl having up to six carbon atoms, optionally substituted by one or more halogen;

b) cycloalkyl having from four to six carbon atoms, optionally bearing one or more substituents selected from the group consisting of $R^6$, halogen, $—CO_2R^7$, $—SR^{71}$ and $—OR^{71}$;

c) cycloalkenyl having five or six carbon atoms, optionally bearing one or more substituents selected from the group consisting of $R^6$, halogen and $—CO_2R^7$; or d) $—(CH_2)_p$-phenyl-$(R^{21})_r$;

$R^1$ is:

hydrogen, chlorine, bromine, fluorine, methyl, methoxy or trifluoromethyl;

$R^2$, $R^3$, $R^4$ and $R^5$, each being the same or different, are:

a) hydrogen;

b) straight- or branched-chain alkyl, alkenyl or alkynyl having up to six carbon atoms, optionally substituted by one or more halogen;

c) straight- or branched-chain alkyl having up to six carbon atoms, substituted by an $—OR^6$ group;

d) halogen;

e) nitro, cyano, $–CO_2R^6$, $—COR^7$, $—X—S(O)_qR^8$, $—S(O)_nR^9$, $—O(CH_2)_mOR^6$, $—NR^{10}R^{11}$, $—CONR^{10}R^{15}$ or $—OR^{61}$;

f) cycloalkyl having from three to six carbon atoms, with the proviso that when $R^2$ is $—S(O)_nR^9$ or $OR^{61}$, then $R^9$ and $R^{61}$ cannot be cycloalkyl with three to six carbon atoms;

with the proviso that when $R^2$ is $—S(O)nR^9$ or $OR^{61}$, then $R^9$ and $R^{61}$ cannot be cycloalkyl with three to six carbon atoms;

$R^6$ is:

a) straight- or branched-chain alkyl, alkenyl or alkynyl having up to six carbon atoms, optionally substituted by one or more halogen; or b) cycloalkyl having from three to six carbon atoms;

$R^{61}$ is:

a) straight- or branched-chain alkyl, alkenyl or alkynyl having up to six carbon atoms, optionally substituted by one or more halogen;

b) cycloalkyl having from three to six carbon atoms;

$R^7$ is:

a) straight- or branched-chain alkyl having up to six carbon atoms, optionally substituted by one or more halogen; or b) cycloalkyl having from three to six carbon atoms;

$R^{71}$ is:

straight- or branched-chain alkyl having up to three carbon atoms;

$R^8$ is:

a) straight- or branched-chain alkyl, alkenyl or alkynyl having up to six carbon atoms, optionally substituted by one or more halogen;

b) cycloalkyl having from three to six carbon atoms;

c) phenyl, optionally substituted by from one to five $R^{21}$ groups, which can be the same or different; or d) $—CH_2CN$, $—CH_2CO_2R^6$ or $—NR^{10}R^{11}$;

$R^9$ is:

a) straight- or branched-chain alkyl, alkenyl or alkynyl having up to six carbon atoms, optionally substituted by one or more halogen;

b) cycloalkyl having from three to six carbon atoms;

c) $—CH_2CN$, $—CH_2CO_2R^6$ or $NR^{10}R^{11}$;

$R^{10}$ is:

a) hydrogen;

b) straight- or branched-chain alkyl having up to six carbon atoms, optionally substituted by one or more halogen; or c) cycloalkyl having from three to six carbon atoms;

provided that when $R^7$ and $R^{10}$ are part of a group $—CONR^7R^{10}$ they can, together with the nitrogen to which they are attached, form a five or six membered ring optionally having one additional hetero ring atom which is oxygen or nitrogen, said ring being optionally substituted by one or more alkyl, each having up to three carbon atoms;

$R^{11}$ is:

a) straight- or branched-chain alkyl having up to six carbon atoms, optionally substituted by one or more halogen;

b) cycloalkyl having from three to six carbon atoms; or c) $—COR^7$, $—CO_2R^7$ or $—CONR^7R^{10}$;

provided that when $R^{10}$ and $R^{11}$ are part of a group $—NR^{10}R^{11}$ they can, together with the nitrogen to which they are attached, form a five or six membered ring optionally having one additional hetero ring atom which is oxygen or nitrogen, said ring being optionally substituted by one or more alkyl, each having up to three carbon atoms;

X is:

oxygen, $—N(R^{12})—$, $—(CR^{13}R^{14}—)_t—$ or $—S(O)_u—$;

$R^{12}$ is:

a) hydrogen;

b) straight- or branched-chain alkyl, alkenyl or alkynyl having up to six carbon atoms, optionally substituted by one or more halogen;

c) cycloalkyl having from three to six carbon atoms;

d) phenyl, optionally substituted by from one to five $R^{21}$ groups, which can be the same or different; or e) $—COR^7$, $—CO_2R^7$, $—CONR^7R^{10}$, $—OR^{17}$ or $—SO_2R^7$;

each of $R^{13}$ and $R^{14}$, which can be the same or different, is:

a) hydrogen; or b) straight- or branched-chain alkyl having up to six carbon atoms, optionally substituted by one or more halogen;

$R^{15}$ is:

$R^7$ or $—OR^{17}$;

provided that when $R^{10}$ and $R^{15}$ are part of a group $—CONR^{10}R^{15}$ they can, together with the nitrogen to which they are attached, form a five or six membered ring optionally having one additional hetero ring atom which is oxygen or nitrogen, said ring being optionally substituted by one or more alkyl, each having up to three carbon atoms;

$R^{17}$ is:

straight- or branched-chain alkyl having up to six carbon atoms;

$R^{21}$ is:

halogen, $R^7$, nitro, cyano, —$CO_2R^7$, —$S(O)_nR^7$, —$NR^{10}R^{11}$ or —$OR^7$;

m is one, two, or three;

n is zero, one or two;

p is zero or one;

q is zero, one or two; provided that when X is —$N(R^{12})$— or oxygen, then q is two and that when X is —S(O)n—, then q is zero or two;

r is zero or an integer from one to five;

t is an integer from one to four, provided that when t is greater than one, the groups —$(CR^{13}R^{14})$— can be the same or different; and u is zero or two;

with the proviso that when $R^1$, $R^3$, and $R^5$ are hydrogen, $R^4$ is $S(O)nR^9$ and n is two, then $R^9$ is methyl;

i) and $R^2$ is chlorine, then R is the definition other than t-butyl;

ii) and $R^2$ is trifluoromethyl, then R is other than methyl.

also with the proviso that when $R^1$, $R^3$, and $R^5$ are hydrogen, $R^2$ is $S(O)nR^9$, n is 0, $R^9$ is methyl, $R^4$ is chlorine, R is not 3,5-bis(trifluoromethyl)phenyl.

2. A method according to claim 1 wherein:

R is:

a) straight- or branched-chain alkyl, alkenyl or alkynyl having up to four carbon atoms, optionally substituted by one or more halogen;

b) cycloalkyl having from four to six carbon atoms, optionally bearing one or more substituents selected from the group consisting of $R^6$, halogen, —$CO_2R^7$, —$SR^{71}$ and —$OR^{71}$;

c) cycloalkenyl having five or six carbon atoms, optionally bearing one or more substituents selected from the group consisting of $R^6$ and halogen;

$R^1$ and $R^5$ are hydrogen;

$R^2$, $R^3$ and $R^4$ each being the same or different, are:

a) hydrogen;

b) straight- or branched-chain alkyl, alkenyl or alkynyl having up to four carbon atoms, optionally substituted by one or more halogen;

c) straight- or branched-chain alkyl having up to four carbon atoms, substituted by an —$OR^6$ group;

d) halogen;

e) nitro, cyano, —X—$S(O)_qR^8$, —$S(O)_nR^9$, —$NR^{10}R^{11}$ or —$OR^{61}$;

f) cycloalkyl having from three to four carbonatoms;

with the proviso that when $R^2$ is $OR^{61}$, $R^{61}$ cannot be cycloalkyl with three to six carbon atoms;

$R^6$ is:

a) straight- or branched-chain alkyl having up to six carbon atoms, optionally substituted by one or more halogen; or $R^{61}$ is:

a) straight- or branched-chain alkyl having up to four carbon atoms, optionally substituted by one or more halogen;

b) cycloalkyl having from three to six carbon atoms;

$R^7$ is:

a) straight- or branched-chain alkyl having up to four carbon atoms, optionally substituted by one or more halogen; or $R^{71}$ is:

straight- or branched-chain alkyl having up to four carbon atoms;

$R^8$ is:

a) straight- or branched-chain alkyl, alkenyl or alkynyl having up to four carbon atoms, optionally substituted by one or more halogen;

b) phenyl, optionally substituted by from one to five $R^{21}$ groups, which can be the same or different; or $R^9$ is:

a) straight- or branched-chain alkyl, alkenyl or alkynyl having up to four carbon atoms, optionally substituted by one or more halogen;

$R^{10}$ is:

a) hydrogen;

b) straight- or branched-chain alkyl having up to four carbon atoms, optionally substituted by one or more halogen; or c) cycloalkyl having from three to six carbon atoms;

provided that when $R^7$ and $R^{10}$ are part of a group —$CONR^7R^{10}$ they can, together with the nitrogen to which they are attached, form a five or six membered ring optionally having one additional hetero ring atom which is oxygen or nitrogen, said ring being optionally substituted by one or more alkyl, each having up to three carbon atoms;

$R^{11}$ is:

a) straight- or branched-chain alkyl having up to four carbon atoms, optionally substituted by one or more halogen;

b) —$CONR^7R^{10}$;

provided that when $R^{10}$ and $R^{11}$ are part of a group —$NR^{10}R^{11}$ they can, together with the nitrogen to which they are attached, form a five or six membered ring optionally having one additional hetero ring atom which is oxygen or nitrogen, said ring being optionally substituted by one or more alkyl, each having up to three carbon atoms;

X is:

—$N(R^{12})$— or —$(CR^{13}R^{14}—)_t$—;

$R^{12}$ is:

a) hydrogen;

b) straight- or branched-chain alkyl having up to four carbon atoms, optionally substituted by one or more halogen;

c) cycloalkyl having from three to six carbon atoms;

d) phenyl, optionally substituted by from one to five $R^{21}$ groups, which can be the same or different;

each of $R^{13}$ and $R^{14}$, which can be the same or different, is:

a) hydrogen; or b) straight- or branched-chain alkyl having up to four carbon atoms, optionally substituted by one or more halogen;

$R^{21}$ is:

halogen, $R^7$, nitro, cyano,—$S(O)_nR^7$, or—$OR^7$;

n is zero, one or two;

q is zero, one or two; provided that when X is —$N(R^{12})$—, then q is two;

t is an integer from one to four, provided that when t is greater than one, the groups —$(CR^{13}R^{14})$— can be the same or different; and with the proviso that when $R^3$ is hydrogen, $R^4$ is $S(O)nR^9$, n is two, $R^9$ is methyl i) and $R^2$ is chlorine, then R is the definition other than t-butyl;

ii) and $R^2$ is trifluoromethyl, then R is other than methyl.

3. A method according to claim 2 wherein:

R is:

a) straight- or branched-chain alkyl, alkenyl or alkynyl having up to four carbon atoms, optionally substituted by one or more halogen;

$R^2$, $R^3$ and $R^4$, each being the same or different, are:

a) hydrogen;

b) straight- or branched-chain alkyl having up to three carbon atoms, optionally substituted by one or more halogen;

c) halogen;

d) nitro, cyano, —S(O)n$R^9$, or —$OR^{61}$;

$R^9$ is:

a) straight- or branched-chain alkyl, alkenyl or alkynyl having up to three carbon atoms, optionally substituted by one or more halogen;

$R^{61}$ is straight- or branched alkyl having up to three carbon atoms, optionally substituted by one or more halogen;

n is zero, one or two;

with the proviso that when $R^3$ is hydrogen, $R^4$ is S(O)n$R^9$, n is two, $R^9$ is methyl i) $R^2$ is chlorine, R is the definition other than t-butyl;

ii) $R^2$ is trifluoromethyl, R is other than methyl.

4. A method according to claim 1 wherein the compound is:

a) 1-(4-chloro-2-methylsulfonylphenyl)-2-cyano-4-methylpentan-1,3-dione; or b) 1-(4-chloro-2-nitrophenyl)-2-cyano-4-methylpentan-1,3-dione.

5. A composition for controlling insects, aphids, mites or nematode pests at a locus formulated for application to the locus of said pest and comprising an effective amount of the compound of anyone of claims 1 to 4.

* * * * *